United States Patent [19]

Day

[11] Patent Number: 5,102,664
[45] Date of Patent: Apr. 7, 1992

[54] GOOD-TASTING GRITTY DRUG FORMULATIONS

[76] Inventor: Charles E. Day, 1224 Bear Creek Rd., Leitchfield, Ky. 42754

[21] Appl. No.: 382,486

[22] Filed: Jul. 19, 1989

[51] Int. Cl.⁵ .................................................. A61K 9/68
[52] U.S. Cl. ..................................... 424/440; 424/439; 424/441; 424/501; 514/974; 514/948; 514/951
[58] Field of Search .................. 424/439, 440, 441, 79, 424/501; 514/974, 948, 951

[56] References Cited

U.S. PATENT DOCUMENTS

| | | | |
|---|---|---|---|
| 1,598,348 | 8/1926 | Hickey | 424/439 |
| 3,794,741 | 2/1974 | Weigle | 426/156 |
| 3,974,272 | 8/1976 | Polli et al. | 424/78 |
| 4,565,702 | 1/1986 | Morley et al. | 426/93 |
| 4,747,881 | 5/1988 | Shaw et al. | 106/209 |
| 4,851,392 | 7/1989 | Shaw et al. | 424/441 X |
| 4,950,140 | 8/1990 | Pflauner et al. | 424/439 |

FOREIGN PATENT DOCUMENTS

| | | |
|---|---|---|
| 1150212 | 7/1983 | Canada. |
| 2344090 | 3/1974 | Fed. Rep. of Germany. |
| 0002651 | of 1884 | United Kingdom ................ 424/439 |

OTHER PUBLICATIONS

"Low Density Lipoproteins", pp. 421-438, Plenum Press (1976).
C.A. 102: 84,412w (1985).
C.A. 108: 210,223z (1988).
C.A. 105: 12,144z (1986).
C.A. 108: 26,960m (1988).
C.A. 100: 109,108a (1984).

*Primary Examiner*—Thurman K. Page
*Assistant Examiner*—Donald R. McPhail
*Attorney, Agent, or Firm*—Gordon W. Hueschen

[57] ABSTRACT

The application discloses a good-tasting and palatable gritty drug formulation, wherein the grittiness is associated as a part of a pleasurable organoleptic sensation, which contains a gritty and optionally bad-tasting or odoriferous drug and a seedy fibrous fruit, and optionally an aqueous medium and a gelling agent, and preferably also a sweetener and a flavoring agent, wherein the gritty drug is representatively an antihypercholesterolemic drug, especially a bile acid sequestrant, and particularly cholestyramine, a method for the preparation thereof, and a method of converting a gritty drug into a more readily-acceptable formulation which assists with patient compliance.

41 Claims, 1 Drawing Sheet

GOOD-TASTING GRITTY DRUG FORMULATIONS

FIELD OF INVENTION

Formulations of drugs which are gritty in order to make them good tasting, pleasing, tolerable, and palatable.

BACKGROUND OF THE INVENTION AND PRIOR ART

Cholestyramine is a high molecular weight, cationic polymer which binds anionic bile acids in the gastrointestinal tract and prevents their reabsorption. Since cholestyramine is neither degraded nor absorbed, it causes bile acids with which it binds to be excreted. This cholestyramine-induced loss of bile acids from the enterohepatic bile acid pool stimulates the liver to replenish the supply via synthesis de novo from cholesterol thereby reducing hepatic intracellular cholesterol. Subsequently, synthesis of hepatic high affinity receptors for apolipoprotein B is stimulated to sequester low density lipoproteins from the plasma to replenish intracellular cholesterol levels since low density lipoproteins are comprised largely of cholesterol. This is the cascade of events which causes plasma cholesterol to be reduced by the binding of bile acids to cholestyramine in the gastrointestinal tract.

Even more important is that cholestyramine selectively reduces the "bad" cholesterol (low density lipoprotein cholesterol) that causes atherosclerosis (C. E. Day, In "Low Density Lipoproteins", edited by C. E. Day and R. S. Levy, Plenum Press, New York, pp. 421-438, 1976). Consequently, cholestyramine eventually inhibits development of atherosclerotic lesions by binding to bile acids in the intestine. Furthermore, atherosclerosis is the primary cause for heart attacks and sudden cardiac death. So, ultimately, the simple act of sequestering bile acids in the gut by cholestyramine leads to a significant reduction not only in plasma cholesterol and low density lipoproteins but also to reductions in morbidity and mortality from cardiovascular disease (JAMA 251: 351-374, 1984), which is the leading cause of death in the U.S.

In addition to its proven efficacy for reducing cardiovascular morbidity and mortality, cholestyramine also has an excellent record of safety (JAMA 251:351-374, 1984). Since the polymer is neither degraded nor absorbed in the intestinal tract, it exhibits no systemic toxicities. Because of its proven record of both safety and efficacy and its well understood mechanism of action, it is not unreasonable to regard cholestyramine as a cure for atherosclerotic disease (C. E. Day, In "The Cholesterol Connection", Artery Press, Fulton, pp. 99-107, 1987) if it were appropriately utilized by patients with elevated cholesterol levels.

Although possessing several very meritorious therapeutic properties, cholestyramine also possesses several handicaps which have precluded widespread implementation of prophylactic and therapeutic administration of this drug for the prevention and treatment of atherosclerotic cardiovascular disease. Patient compliance in the long-term administration of cholestyramine is relatively poor (JAMA 251: 351-374, 1984). People find it objectionable to adhere to prolonged administration of cholestyramine for several reasons.

One shortcoming which contributes to poor patient compliance is the lack of potency with the recommended daily dose being 4 to 24 grams per day. The drug also has an objectionable taste and odor. Additionally, the physical form of the drug is a tiny plastic bead which has a gritty mouthfeel. Because of the bulk which must be consumed, among other factors, cholestyramine may cause in many patients a number of uncomfortable gastrointestinal side effects such as bloating, nausea, constipation, or gas. For patients in whom constipation may be a barrier to consumption of cholestyramine, many physicians recommend concurrent administration of a bulk laxative such as psyllium hydrocolloid. Although aiding in the relief or prevention of constipation, this simply requires the patient to now consume two instead of one bulky gritty material.

Cholestyramine was originally marketed under the brand name Cuemid(®), essentially as the pure bulk drug which could be stirred in a glass of water, fruit juice, or other appropriate liquid, and consumed. However, the smell and taste of the bulk drug is so objectionable (the malodorous component being trimethylamine, one of the essential fragrances of rotten fish) that Cuemid(®) had very low patient acceptance. This taste and odor was successfully masked with flavors and sweeteners in the Questran(®) formulation which currently is the market standard.

The Questran(®) formulation, or any other presently-available formulation, does not successfully address the problem of the objectionable gritty nature of cholestyramine. However, several attempts have been made unsuccessfully to create palatable compositions. One such attempt is reported in U.S. Pat. No. 3,974,272 in which the composition is comprised of an aqueous medium (water, milk, or fruit juice), cellulosic material, alginate, and cholestyramine. A similar approach to conceal the grittiness is described in European Patent Application EP 251,369 in which a combination of cholestyramine, antimicrobial agent, suspending agent, and coating agent is used to improve the palatability of the resin. European Patent Application EP 177,368 describes a hydrophobic matrix consisting of fatty acids, natural or synthetic waxes or mixtures thereof, and a glyceride, which helps to physically mask the unpleasant taste of cholestyramine. In a similar vein European Patent Application EP 227,603 describes a chewable drug delivery system in which cholestyramine is coated with lecithin or glycerides or polyalkylene glycols and a confectionary matrix to improve the palatability of the drug. U.S. Pat. No. 4,565,702 coats insoluble fiber with soluble fiber such as pectin or alginate. German Offen. 2,344,090 describes a cholestyramine-containing coacervate comprised of cholestyramine, modified cellulose, lactose and flavor to mask the grittiness and improve taste characteristics of the drug. An ingestible aggregate and delivery system is detailed in U.S. Pat. No. 4,747,881 in which the cholestyramine bead is coated with a preswelled hydrocolloid and dried to form aggregates of coated beads in which hydration is delayed. These aggregates can be ingested and chewed so that prehydration is not required as in formulations of cholestyramine such as Questran(®) U.S. Pat. No. 4,404,346 and Canadian Patent 1,150,212 describe a process for comminution of cholestyramine beads to produce a powder which forms stable dispersions and does not have a gritty taste.

All previous attempts to overcome the grittiness problem with cholestyramine and similar gritty drugs have one underlying characteristic. Each has been an attempt to physically conceal, alter, mask, eliminate, or modify the gritty nature and texture of the drug. The nature of the present invention is to capitalize on the gritty characteristic of cholestyramine and similar gritty drugs to create a formulation which is not only acceptable to the patient but pleasant as well.

BRIEF DESCRIPTION OF THE DRAWINGS

A more complete understanding of the invention may be had by reference to the following detailed description of the invention when taken in conjunction with the accompanying drawing, wherein FIGS. 1, 2, and 3 all show a representative formulation according to the invention.

OBJECTS OF THE INVENTION

Figure 1:
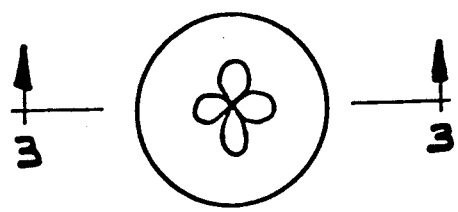
FIG. 1 shows a top view thereof.

It is an object of the present invention to provide a good-tasting gritty drug formulation which is at one and the same time effective, tolerable, palatable, and pleasing to the taste. It is a further object of the invention to provide such a gritty drug formulation wherein the gritty drug comprises cholestyramine or another antihypercholesterolemic drug, especially a bile acid sequestrant drug. Another object of the invention is the provision of a method for the preparation of such a good-tasting gritty drug formulation. Yet another object of the invention is the provision of such a method wherein the gritty drug is cholestyramine or another antihypercholesterolemic drug, especially a bile acid sequestrant drug. A further object is the provision of a superior method of orally administering a gritty drug by first converting the same into a formulation of the present invention and then orally administering the drug in such improved and good-tasting form. Additional objects of the invention will become apparent hereinafter, and still others will be obvious to one skilled in the art to which this invention pertains as the description proceeds.

SUMMARY OF THE INVENTION

The invention, then, comprises the following, inter alia, alone or in combination:

A good-tasting and palatable gritty drug formulation, wherein the grittiness is associated as a part of a pleasurable organoleptic sensation, consisting essentially of a gritty and optionally bad-tasting or odoriferous drug, and a seedy fibrous fruit; such a formulation comprising also an aqueous medium and a gelling agent, and optionally a sweetener and/or a flavoring agent; such a formulation wherein the gritty drug is cholestyramine; such a formulation wherein the seedy fibrous fruit is strawberry; such a formulation wherein the gelling agent is pectin; such a formulation wherein the aqueous medium is selected from the group consisting of water, artificial fruit juice, and natural fruit juice; such a formulation wherein the gritty drug is cholestyramine, the aqueous medium is water, the seedy fibrous fruit is a berry fruit, and wherein the gelling agent is pectin. Also, such a formulation wherein the formulation is presented in the form of a candy having an exterior confectionary coating; such a formulation wherein the exterior confectionary coating is a chocolate coating; such a formulation wherein the gritty drug is an antihypercholesterolemic drug; and such a formulation wherein the gritty drug is a bile acid sequestrant.

Moreover, a method for the preparation of a good-tasting and palatable gritty drug formulation, wherein the grittiness is associated as a part of a pleasurable organoleptic sensation, comprising the following:

a gritty and optionally bad tasting or odoriferous drug, a seedy fibrous fruit, an aqueous medium, and a gelling agent, and optionally a sweetener and/or a flavoring agent, which comprises the step of mixing together the selected gritty drug, a gelling agent, a seedy fibrous fruit, an aqueous medium, and optionally a sweetening agent and/or a flavoring agent, mixing the materials together thoroughly, thereby to provide a mobile gel of variable consistency, controlling the consistency by controlling the amount of the aqueous medium employed, and presenting and packaging the same in the form of a good-tasting palatable gritty drug formulation which is more acceptable to the patient and which accordingly assists in patient compliance with an established dosage regimen for the drug; such a method wherein the gritty drug is cholestyramine; such a method wherein the seedy fibrous fruit is strawberry; such a method wherein the gelling agent is pectin; such a method wherein the aqueous medium is selected from the group consisting of water, artificial fruit juice, and natural fruit juice; such a method wherein the gritty drug is cholestyramine, the aqueous medium is water, the seedy fibrous fruit is strawberry, and wherein the gelling agent is pectin; such a method wherein the gritty drug is an antihypercholesterolemic drug; such a method wherein the gritty drug is a bile acid sequestrant; such a method wherein the formulation is presented in the form of a candy having an exterior confectionary coating; such a method wherein the exterior confectionary coating is a chocolate coating; such a method wherein the seedy fibrous fruit is strawberry; and such a method wherein the amount of the drug in each of the candies is approximately one third ($\frac{1}{3}$) to one twelfth (1/12) of the recommended daily dose for the drug.

Moreover, such a good-tasting gritty drug formulation wherein the amount of the drug in each of the candies or other unit dosage is approximately one third ($\frac{1}{3}$) to one twelfth (1/12) of the recommended daily dose for the drug; and such a formulation wherein the drug is cholestyramine and wherein the amount of the drug in each of the candies or other unit dosages is approximately 1000 to 1500 milligrams.

Further, a method of modifying a gritty drug prior to oral administration of the same which comprises the step of first converting the same into any formulation as set forth in the foregoing for purposes of increasing palatability and patient acceptance thereof; such a method wherein the gritty drug is an antihypercholesterolemic drug, preferably a bile acid sequestrant, and especially cholestyramine.

GENERAL DESCRIPTION AND NATURE OF THE INVENTION

This invention makes no attempt to physically mask, conceal, or in any way alter the grittiness of cholestyramine. Rather it takes advantage of the grittiness of the drug to create good tasting formulations which simulate pleasant food experiences with which people already associate grittiness as part of a pleasurable organoleptic sensation. Therefore, the nature of this invention is a psychological rather than a physical masking of the gritty nature of cholestyramine to create a drug dosage form which is actually a taste treat to the patient.

The nature of this invention is to simulate the taste and texture of a seedy fibrous fruit by combining the drug with a seedy fibrous fruit and by utilizing the gritty drug itself as one of the components to impart the seedy fibrous texture to the composition. These are essential ingredients. For greater adaptability and elegance, other ingredients are also added and, for the most elegant presentation, two additional components may also be considered essential. These two additional components of the composition are an aqueous medium such as water or a natural or artificial fruit juice and a gelling agent, with sweeteners and flavoring agents being additional preferred but only optional components.

Seedy fibrous fruits are commonly used to make jams, preserves, cookie and pie fillings, cobblers, conserves, chutneys, sweetmeats, candies and other confections. Seedy fibrous fruits from which tasty sweets and confections can be prepared and which are appropriate for simulation with this invention include strawberries, raspberries, blackberries, and other seedy fruits listed in TABLE 1. Gelling agents include but are not limited to pectin, guar gum, locust bean gum, and other agents listed in TABLE 2. Flavoring agents are those agents known in the art which impart the flavor characteristics of the seedy fruit composition to be simulated. Sweeteners include sucrose, glucose, fructose, saccharin, xylitol, sorbitol, mannitol, aspartame, alitame, acesulfame, or other such agents.

The cholestyramine simulation of seedy fibrous fruit compositions can be presented in the form of a filling for candies, cookies, pies, cakes, tarts, and other confections, or a spread for crackers, bread, cookies, cakes, etc. It can imitate a seedy fruit jam, preserve, etc. and can be packaged in bottles, jars, cans, foil or plastic pouches, cups, tubs, or other suitable containers.

This invention can also be applied in similar fashion to drugs other than cholestyramine which also are gritty. These may include, but are not limited to, other bile acid sequestrants or antihypercholesterolemic drugs such as colestipol, divistyramine, or polidexide, antacids or mineral supplements such as calcium carbonate, and bulk laxatives such as psyllium hydrocolloid.

DETAILED DESCRIPTION OF THE INVENTION

The following Examples are given to illustrate the method and the formulations of the present invention, but are not to be construed as limiting:

EXAMPLE 1

STRAWBERRY SPREAD OR FILLING MADE WITH CHOLESTYRAMINE TO SIMULATE THE SEEDY CHARACTER OF STRAWBERRIES

Dry mix the following materials in the listed amounts:
4.0 grams cholestyramine USP
2.0 grams apple pectin
400 milligrams spray-dried strawberry flavor
200 milligrams aspartame Add:
1.0 milliliter imitation strawberry flavor
20.00 milliliters distilled water
Mix immediately and thoroughly and add:
10 grams strawberry preserve
Mix thoroughly.

The product is a mobile gel of the consistency of a heavy jam or the filling of a chocolate-covered candy, and its viscosity and degree of solidity can be readily controlled by varying the amount of water (or natural or artificial fruit juice which may be substituted therefor) employed.

This strawberry composition can be used as a filling for candies, e.g., chocolate strawberry creams, or other confections, or as a spread for crackers, breads, and the like.

Figure 2:
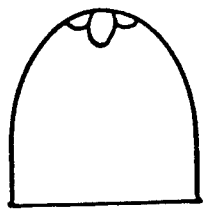
FIG. 2 shows a side or elevation view thereof.
Figure 3:
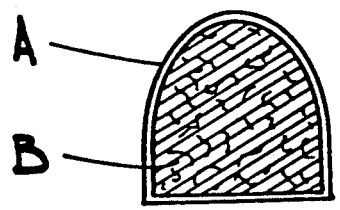
FIG. 3 shows a cross-section thereof along line 3-3 of FIG. 1, showing a formulation of the invention B containing the gritty drug particles therein, coated or packaged for consumption in a chocolate shell A, thereby comprising a totally-packaged, consumable, palatable and good-tasting gritty drug formulation of the invention.

Although presentation of the gritty drug formulation of the present invention can take many forms, one edible confectionary type of presentation is illustrated in FIGS. 1-3. A thin shell of melted milk chocolate A is applied to an appropriately-shaped mold and allowed to solidify. The cavity of the milk chocolate shell in the mold is filled to capacity with the semi-solid gritty drug formulation B of the present invention. The bottom of the chocolate shell and its drug contents are sealed with a further portion of the melted milk chocolate shell A, which is also allowed to solidify. The milk chocolate shell A filled with gritty drug formulation B is then released from the mold, and said drug formulation is now presented in a readily-comestible form. This is but one example of many creative and palatable ways in which the drug formulations of this invention can be presented for pleasing and tolerable human consumption.

Other forms of presentation of the cholestyramine formulation of Example 1 include cookies, pies, cakes, tarts, and other confections, or as a spread for crackers, bread, cookies, cakes, and the like. It can likewise be incorporated into a seedy fibrous fruit jam, preserve, or the like, and it may ultimately be packaged in bottles, jars, cans, foil or plastic pouches, cups, tubs, or other suitable containers.

One particularly suitable form of packaging of the formulation of the invention is in plastic pouches in the form of a pudding or pie filling mix, which if desired can readily be incorporated into a pie crust in the usual manner now employed for the production of pies from prepared pie crust mixes or prepared pie crust "ready mades", the ultimate product in any case being palatable, tolerable, pleasing to the taste, and totally acceptable as an innocuous and superior manner of administering the otherwise objectionable and gritty drug cholestyramine.

Each of the candies of the FIGS contains approximately 1000 to 1500 milligrams of the drug cholestyramine, so that an acceptable daily dose involves the ingestion of three (3) of the cholestyramine candies prepared as in the foregoing, three (3) times a day. Higher or lower concentrations of drug may be incorporated into each unit or piece of candy or the like, so that, e.g., even a single piece or three (3) pieces constitute a minimum daily dose or as many as, e.g., twelve (12) pieces or units constitute a minimum daily dose of drug. This provides a totally satisfactory daily dosage of the gritty drug cholestyramine, but presented in a pleasing, palatable, and taste-acceptable form, thus making it easier for the patient to comply with the dosage regimens already well established for the effectiveness of the drug.

When presented in the chocolate-coated candy form more fully described in the foregoing and in the drawings, each candy unit can if desired be designed to contain all, but preferably between one third (⅓) and one twelfth (1/12) of the daily dosage regimen for the drug, thereby enabling a patient to comply with the required or suggested daily dosage regimen by ingesting a single one or between about three and about twelve of the candy units per day, usually divided into one or more, but usually three or four, individual or unit dosages which, as the drug is now constituted, may be more properly referred to as one or three or four pleasurable taste experiences.

Similarly, when packaged in the form of jams, pie fillings, or the like, to name a few, it is a simple matter to calculate and designate the drug content of the formulation of the present invention, however presented in whatever form and however packaged, so that compliance of the patient with the minimum daily dosage requirements for full effectiveness of the drug is readily observed and maintained.

EXAMPLE 2

The practice of Example 1 is repeated with gritty drugs other than cholestyramine. In the case of colestipol, divistyramine, or polidexide, the product is equally useful and useful for the same purpose as the cholestyramine-containing products of Example 1.

EXAMPLE 3

The practice of Example 1 is repeated using, instead of the gritty drug cholestyramine, antacids or mineral supplements such as calcium carbonate, or a bulk laxative such as psyllium hydrocolloid. In each case, the product is found to be acceptable, palatable, and pleasing to the taste, and entirely suitable as a manner of administering the otherwise objectionable gritty drug.

EXAMPLE 4

The practice of Example 1, 2, or 3 is repeated using other seedy fruits of TABLE 1 and corresponding fruit flavors with equally satisfactory results.

EXAMPLE 5

The practice of Example 1, 2, 3, or 4 is repeated using other gelling agents of TABLE 2 with equally satisfactory results.

EXAMPLE 6

The practice of any of the previous Examples is repeated using only the gritty drug plus the gritty fibrous fruit as components of the composition. Although this presents a definite improvement as to taste and acceptability, inclusion of the gelling agent and the aqueous medium or a fruit juice corresponding to the fruit employed adds much to the elegance of the taste sensation and acceptability. Finally, addition of a touch of sweetener and flavor corresponding to the fruit employed, or sometimes citric acid for tartness, optimizes the psychological effect and heightens the taste sensation even further.

TABLE 1

NON-COMPREHENSIVE, NON-INCLUSIVE LIST OF SEEDY FRUITS FOR WHICH CHOLESTYRAMINE CAN BE USED TO SIMULATE SEEDY COMPOSITIONS

| Seedy Fruit |
| --- |
| Strawberry |

TABLE 1-continued

NON-COMPREHENSIVE, NON-INCLUSIVE LIST OF SEEDY FRUITS FOR WHICH CHOLESTYRAMINE CAN BE USED TO SIMULATE SEEDY COMPOSITIONS

| Seedy Fruit |
| --- |
| Raspberry |
| Blackberry |
| Boysenberry |
| Loganberry |
| Dewberry |
| Gooseberry |
| Cranberry |
| Mulberry |
| Elderberry |
| Blueberry |
| Fig |
| Currant |
| Kiwi |

TABLE 2

NON-COMPREHENSIVE, NON-INCLUSIVE LIST OF GELLING AGENTS USEFUL IN CHOLESTYRAMINE SEEDY FRUIT COMPOSITIONS

| Gelling Agent |
| --- |
| Pectin |
| Guar gum |
| Xanthan gum |
| Gum arabic |
| Gum acacia |
| Locust bean gum |
| Carageenan |
| Alginic acid |
| Psyllium hydrocolloid |
| Oat bran gum |
| Rice bran gum |
| Glucomannan |
| Tragacanth gum |
| Karaya gum |
| Tapioca |
| Corn starch |
| Cellulose gums |
| Agar |
| Gelatin |

It is therefore seen that the present invention provides a novel good-tasting gritty drug formulation, which may be presented in many acceptable ways, and packaged in any suitable manner, as well as a method for the preparation and use of such palatable and good-tasting drug formulations, all having the unpredictable and highly advantageous characteristics and effects as more fully set forth in the foregoing, and whereby all of the objectives of the present invention are attained.

It is to be understood that the invention is not to be limited to the exact details of operation, or to the exact compositions, methods, procedures, or embodiments shown and described, as obvious modifications and equivalents will be apparent to one skilled in the art, and the invention is therefore to be limited only by the full scope which can be legally accorded to the appended claims.

I claim:

1. A palatable gritty drug formulation, wherein the grittiness is associated as a part of an organoleptic taste sensation, consisting essentially of the following:
    (a) a pharmaceutically effective amount of a gritty drug, selected from the group consisting of bile acid sequestrants, antihypercholesterolemics, antacids, mineral supplements, and bulk laxatives and
    (b) a seedy fibrous fruit, (a) and (b) being admixed together, the formulation being in the form of a gel.

2. A formulation of claim 1, comprising also an aqueous medium and a gelling agent, and optionally a sweetener and/or a flavoring agent, the formulation being in the form of a viscous gel.

3. A good-tasting drug formulation of claim 2 wherein the gritty drug is cholestyramine.

4. A drug formulation of claim 3, wherein the seedy fibrous fruit is strawberry.

5. A drug formulation of claim 4, wherein the gelling agent is pectin.

6. A drug formulation of claim 2, wherein the aqueous medium is selected from the group consisting of water, artificial fruit juice, and natural fruit juice.

7. A drug formulation of claim 2, wherein the gritty drug is cholestyramine, the aqueous medium is water, the seedy fibrous fruit is a berry fruit, and wherein the gelling agent is pectin.

8. A drug formulation of claim 2, wherein the formulation is presented in the form of a candy having an exterior confectionary coating.

9. A drug formulation of claim 8, wherein the exterior confectionary coating is a chocolate coating.

10. A drug formulation of claim 7, wherein the formulation is presented in the form of a candy having an exterior confectionary coating.

11. A drug formulation of claim 7, wherein the exterior confectionary coating is a chocolate coating.

12. A drug formulation of claim 2, wherein the seedy fibrous fruit is strawberry.

13. A drug formulation of claim 2, wherein the gritty drug is an antihypercholesterolemic drug.

14. A drug formulation of claim 13, wherein the gritty drug is a bile acid sequestrant.

15. Method for the preparation of a palatable gritty drug formulation, wherein the grittiness is associated as a part of an organoleptic taste sensation, comprising the following: a pharmaceutically-effective amount of a gritty drug selected from the group consisting of bile acid sequestrants, antihypercholesterolemics, antacide, mineral supplements and bulk laxatives, a seedy fibrous fruit, an aqueous medium, and a gelling agent, and optionally a sweetener and/or a flavoring agent, which comprises the step of mixing together the selected gritty drug, a gelling agent, a seedy fibrous fruit, an aqueous medium, and optionally a sweetening agent and/or a flavoring agent, thereby to provide a gel of variable consistency, controlling the consistency by controlling the amount of the aqueous medium employed, and presenting the same in the form of a gritty drug formulation which has improved palatability and which accordingly assists in patient compliance with an established dosage regimen for the drug.

16. The method of preparing a drug formulation of claim 15, wherein the gritty drug is cholestyramine.

17. The method of preparing a drug formulation of claim 15, wherein the seedy fibrous fruit is strawberry.

18. The method of preparing a drug formulation of claim 15, wherein the gelling agent is pectin.

19. The method of preparing a drug formulation of claim 15, wherein the aqueous medium is selected from the group consisting of water, artificial fruit juice, and natural fruit juice.

20. The method of preparing a drug formulation of claim 15, wherein the gritty drug is cholestyramine, the aqueous medium is water, the seedy fibrous fruit is strawberry, and wherein the gelling agent is pectin.

21. The method of preparing a drug formulation of claim 15, wherein the formulation is presented in the form of a candy having an exterior confectionary coating.

22. The method of preparing a drug formulation of claim 21, wherein the exterior confectionary coating is a chocolate coating.

23. The method of preparing a drug formulation of claim 15, wherein the gritty drug is an antihypercholesterolemic drug.

24. The method of preparing a drug formulation of claim 23, wherein the gritty drug is a bile acid sequestrant.

25. The method of preparing a drug formulation of claim 23, wherein the formulation is presented in the form of a candy having an exterior confectionary coating.

26. The method of preparing a drug formulation of claim 25, wherein the exterior confectionary coating is a chocolate coating.

27. The method of preparing a drug formulation of claim 23, wherein the seedy fibrous fruit is strawberry.

28. The method of preparing a drug formulation of claim 21, wherein the amount of the drug in each of the candies is approximately one third ($\frac{1}{3}$) to one twelfth (1/12) of the recommended daily dose for the drug.

29. The method of preparing a drug formulation of claim 25, wherein the amount of the drug in each of the candies is approximately one third ($\frac{1}{3}$) to one twelfth (1/12) of the recommended daily dose for the drug.

30. The method of preparing a drug formulation of claim 26, wherein the amount of the drug in each of the candies is approximately one third ($\frac{1}{3}$) to one twelfth (1/12) of the recommended daily dose for the drug.

31. A drug formulation of claim 8, wherein the amount of the drug in each of the candies is approximately one third ($\frac{1}{3}$) to one twelfth (1/12) of the recommended daily dose for the drug.

32. A drug formulation of claim 8, wherein the drug is cholestyramine and wherein the amount of the drug in each of the candies is approximately 1000 to 1500 milligrams.

33. A method of modifying a gritty drug prior to oral administration of the same which comprises the step of first converting the same into a formulation of claim 1 for purposes of improving palatability and patient acceptance thereof.

34. A method of modifying a gritty drug prior to oral administration of the same which comprises the step of first converting the same into a formulation of claim 2 for purposes of improving palatability and patient acceptance thereof.

35. The method of claim 33 wherein the drug is an antihypercholesterolemic agent.

36. The method of claim 35 wherein the drug is a bile acid sequestrant.

37. The method of claim 36 wherein the drug is cholestyramine.

38. The method of claim 34 wherein the drug is an antihypercholesterolemic agent.

39. The method of claim 38 wherein the drug is a bile acid sequestrant.

40. The method of claim 39 wherein the drug is cholestyramine.

41. Method for the preparation of a good-tasting and palatable gritty drug formulation of claim 1, which consists essentially of the step of mixing together the selected gritty drug and the seedy fibrous fruit.

* * * * *

UNITED STATES PATENT AND TRADEMARK OFFICE
CERTIFICATE OF CORRECTION

PATENT NO. : 5,102,664
DATED : Apr. 7, 1992
INVENTOR(S) : Charles E. Day

It is certified that error appears in the above-identified patent and that said Letters Patent is hereby corrected as shown below:

```
Title Page, [56] References Cited, U.S. PATENT DOCUMENTS, last
   listing; "Pflauner" should read -- Pflaumer --.

Column 5, last line; move "Add:" at the end of line 68 to the top
   of Column 6 and insert as the first line.
Column 8, line 63; "pharmaceutically effective" should read
   -- pharmaceutically-effective --.

Column 8, line 66; "laxatives and" should read -- laxatives,
   and --.
Column 9, line 5; delete "good-tasting".
Column 9, line 5,6; "2 wherein" should read -- 2, wherein --.
Column 9, approximately line 40; "antacide," should read
   -- antacids, --.
Column 9, line 41; "supplements and" should read
   --supplements, and--.
```

Signed and Sealed this

Twenty-eighth Day of September, 1993

Attest:

BRUCE LEHMAN

*Attesting Officer*   *Commissioner of Patents and Trademarks*